United States Patent
Raynor et al.

(10) Patent No.: US 8,120,689 B2
(45) Date of Patent: Feb. 21, 2012

(54) REFERENCE DATA ENCODING IN IMAGE SENSORS

(75) Inventors: Jeffrey Raynor, Lothian (GB); Patrick Baxter, Lothian (GB)

(73) Assignee: STMicroelectronics (Research & Development) Limited, Marlow-Buckinghamshire (GB)

( * ) Notice: Subject to any disclaimer, the term of this patent is extended or adjusted under 35 U.S.C. 154(b) by 476 days.

(21) Appl. No.: 12/432,036

(22) Filed: Apr. 29, 2009

(65) Prior Publication Data

US 2009/0273692 A1    Nov. 5, 2009

(30) Foreign Application Priority Data

May 2, 2008 (EP) ................................ 08155615

(51) Int. Cl.
*H04N 5/335* (2011.01)
(52) U.S. Cl. ....................................................... 348/310
(58) Field of Classification Search ........... 348/308–310
See application file for complete search history.

(56) References Cited

U.S. PATENT DOCUMENTS

| 5,465,114 A | 11/1995 | Miyamoto | 348/80 |
| 2005/0014201 A1* | 1/2005 | Deutsch | 435/7.2 |
| 2006/0063286 A1 | 3/2006 | Bidermann et al. | 438/17 |

FOREIGN PATENT DOCUMENTS

EP    1263208    4/2002

* cited by examiner

*Primary Examiner* — Alicia M Harrington
(74) *Attorney, Agent, or Firm* — Allen, Dyer, Doppelt, Milbrath & Gilchrist, P.A.

(57) ABSTRACT

Data is encoded on an image sensor that has a plurality of pixels including one or more bio-sensing pixels and one or more data encoding pixels. The method includes applying a covering material selectively to the data encoding pixels depending on the data to be encoded, the covering material having a detectable difference in opacity relative to having no covering material present. The method includes reading the data encoding pixels, in the presence of light, and decoding data according to a pre-determined scheme depending on the presence of the covering material on the data encoding pixel. As bio-reagents are typically applied after manufacture of the image sensor, the image sensor can have information encoded for electronic detection subsequent to manufacture.

24 Claims, 3 Drawing Sheets

= Covered ID Pixel

REFERENCE DATA ENCODING IN IMAGE SENSORS

FIELD OF THE INVENTION

The present invention relates to the encoding of reference data in image sensors and particularly, but not exclusively, to encoding unique identification data for bio-optical applications.

BACKGROUND OF THE INVENTION

It is known to record reference data on a variety of types of microchips, including image sensors, during manufacture of the microchips. Such detail may include product codes and the like and, may be included in the chip circuitry using a variety of coding schemes. In the case of an image sensor, such reference data may, for example, identify the particular type of the basic sensor chip.

Most bio-optical sensor systems include a bio-sensor made up of an image sensor on to which a biological reagent material is bonded. Typically, the image sensor design and/or fabrication and biological reagent deposition are undertaken by different companies. That is, a silicon manufacturer would design and produce an image sensor and a bio system integrator would deposit the relevant biological reagent material on the pixel array.

Bio-optical sensor systems typically operate by using a biological reagent material which reacts by emitting light in the presence of a particular mechanical or biological substance. However, the image sensor for use in the bio-optical sensor system may be used with a number of different biological reagent materials. Accordingly, a bio-system integrator may use the same image sensor type for depositing a variety of different biological reagent materials depending on the chemical or biological substances which are to be detected.

To ensure that image sensors are not mixed up, identification information may be needed on the sensor. However, it is typically the silicon manufacturer which would add identification information on to the sensor.

SUMMARY OF THE INVENTION

According to a first aspect of the present invention there is provided a method of encoding data on an image sensor, the image sensor comprising a plurality of pixels including one or more bio-sensing pixels and one or more data encoding pixels. The method includes applying a covering material selectively to the data encoding pixels depending on the data to be encoded, the covering material having a detectable difference in opacity relative to having no covering material present. The method includes reading the data encoding pixels, in the presence of light, and decoding data according to a pre-determined scheme depending on the presence of the covering material on the data encoding pixel.

Preferably, the method further comprises applying a biological reagent material to at least one of the bio-sensing pixels. Preferably, the method may further comprise comparing an output of the at least one data encoding pixel to a pre-determined threshold voltage, wherein outputs below the threshold voltage are considered to be a first digital code and outputs above the threshold voltage are considered to be a second digital code for a given pixel integration time.

Preferably, the first digital code is a binary zero and the second digital code is a binary one. Preferably, each pixel of the or each data encoding pixels represents one bit in a digital word. Alternatively, where there is a plurality of data encoding pixels, pre-defined groups of data encoding pixels represent one bit in a digital word.

Preferably, the pre-determined encoding scheme is configured to store one or more of the following: Identification information, batch information, date of deposit of bio-reagent material, expiration date, operation of image sensor information, integration time of image sensor, micro-fluidic control information and/or which biological tests are present.

Preferably, the method further comprises performing a self-test in respect of the data encoding pixels. Preferably, the step of performing a self-test further comprises the step of testing that the data obtained from the or each data encoding pixels is valid based on the pre-determined scheme. Preferably, the pre-determined scheme includes the use of a checksum value and the step of checking further comprises comparing the obtained data with the expected checksum value.

Preferably, the covering material is opaque. Preferably, the covering material is the same as the bio-reagent material.

Preferably, performing a self-test further comprises testing the operation of the bio-reagent material concurrently with testing that data obtained from the data encoding pixels is valid based on the pre-determined scheme. Preferably, testing the operation of the bio-reagent material comprises detecting light emitted by the bio-reagent material with the data encoding pixels. Preferably, testing the operation of the bio-reagent material further comprises inferring the shelf-life of the bio-reagent material based on the quantity of light emitted by the bio-reagent material.

According to a second aspect of the present invention there is provided an image sensor including a plurality of pixels comprising one or more bio-sensing pixels and one or more data encoding pixels, and a readout unit or means for reading output pixel values from the plurality of pixels. A determination unit or means is for determining whether the data encoding pixel has been covered by a covering material based on the output pixel values of the data encoding pixels and, based on the presence of the covering material, outputting encoded data. A decoding unit or means is also included. The encoded data is decoded according to a pre-determined scheme.

Preferably, the plurality of pixels, both the bio-sensing pixels and the data encoding pixels, are the same type of pixel. Preferably, the type of pixel is one of a 1T, 3T or 4T. "T", in this context, is a commonly used abbreviation of transistor in the CMOS image sensor technology arena. As such, "1T" refers to a pixel having one transistor, "3T" to a pixel having three transistors and "4T" to a pixel having four transistors. The configuration for 1T, 3T and 4T transistors are known. Alternatively, the bio-sensing pixels are either 1T, 3T or 4T type and the data encoding pixels are of a differential pixel architecture.

A differential pixel architecture is disclosed in European Patent Application 07270014.9 (as yet, not published), the contents of which are incorporated by reference. Preferably, the determination unit or means comprises a comparator to compare one or more pre-determined threshold voltages with the pixel output value.

According to a third aspect of the present invention there is provided a bio-optical sensor including the image sensor described above. According to a fourth aspect of the present invention there is provided a biological reader system comprising such a bio-optical sensor.

Preferably, the biological reader system comprises a validation unit or means to ensure that the bio-optical sensor is validated for use with the system. For example, the validation unit or means may check that the bio-optical sensor is not expired and/or is compatible with the reader system Preferably, the biological reader system comprises a controller or means to control the function of the bio-optical sensor. For example, the controller or means may control the bio-optical sensor integration time and/or microfluidics (the behavior, precise control and manipulation of fluids within the bio-optical sensor).

BRIEF DESCRIPTION OF THE DRAWINGS

Embodiments of the present invention will now be described, by way of example only, with reference to the drawings, in which.

DETAILED DESCRIPTION OF THE PREFERRED EMBODIMENTS

Figure 1:
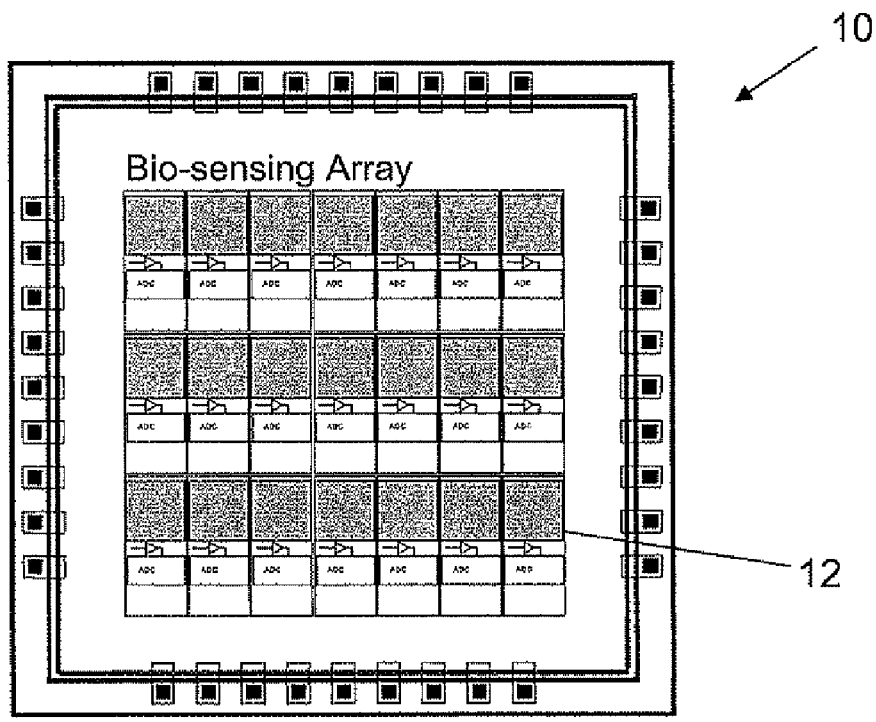
FIG. 1 is a schematic diagram illustrating a bio-optical image sensor in accordance with the prior art.

Referring firstly to FIG. 1, a conventional bio-optical image sensor 10 is shown, comprising a pixel array 12. After manufacture of the image sensor 10, a bio-system integrator can deposit biological reagent materials directly on to the pixel array 12. The pixel array 12 can then be operated to detect light emitted from the bio-reagent material due to the presence of a chemical or biological substance that the reagent material is designed to detect. If the bio-system integrator needs to use more than one biological reagent material or the same type of image sensor, and for the type of material to be automatically detected by any systems connected to the image sensor, identification data must be directly programmed into either the image sensor itself or a custom application specific integrated circuit (ASIC).

Figure 2:
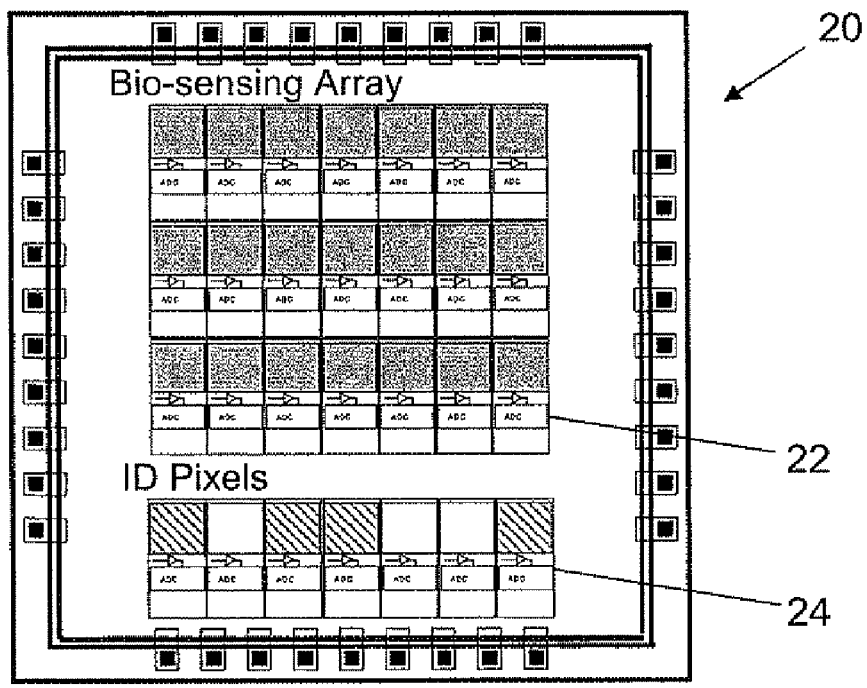
FIG. 2 is a schematic diagram illustrating a bio-optical image sensor incorporating a plurality of identification pixels in accordance with features of the present invention.

Referring now to FIG. 2, an image sensor 20 in accordance with features of the present invention comprises a bio-sensing pixel array 22 and a data encoding pixel array, which in this case is an identification (ID) pixel array 24. With the image sensor 20 of FIG. 2, the bio-systems integrator can deposit a bio-reagent material on the bio sensing array 22 and an opaque or semi-opaque material over one or more of the ID pixels of the ID pixel array 24. In this manner, the system can read out the values of the ID pixels in the presence of light and detect which of the ID pixels have been covered by the opaque or semi-opaque material. In this manner each pixel can represent a single bit of a digital word, with a pixel that is covered representing a binary 0 and a pixel that is uncovered a binary 1, or vice versa.

Accordingly, the bio-systems integrator can pre-determine a scheme or code to apply to the ID pixel array 24 which can then be decoded by specific decoding means or by software to identify the particular biological reagent material which has been deposited on the bio-sensing array 22.

Figure 3:
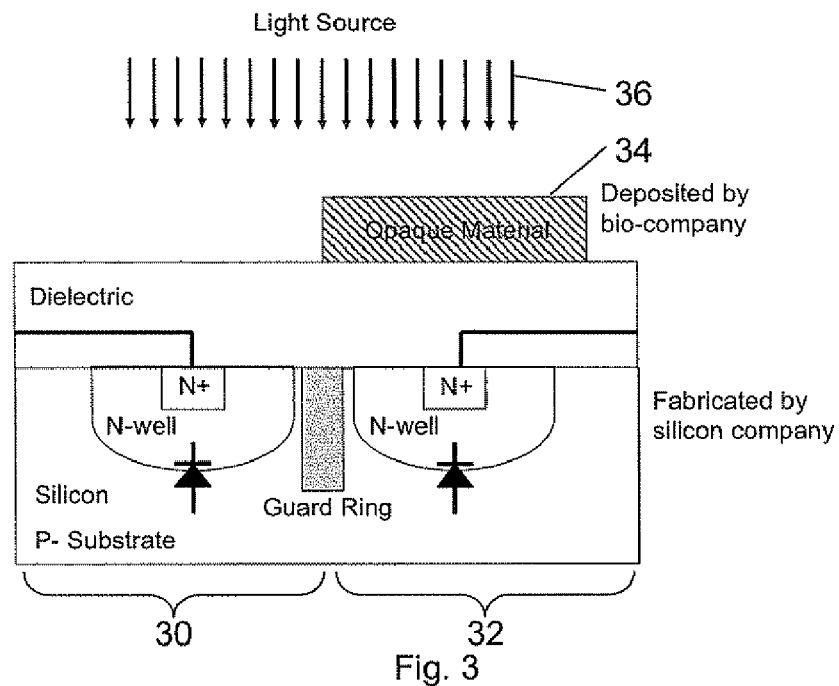
FIG. 3 is a cross-sectional view of two data encoding pixels, as in FIG. 2, one of which is obscured by an opaque material.
Figure 4:
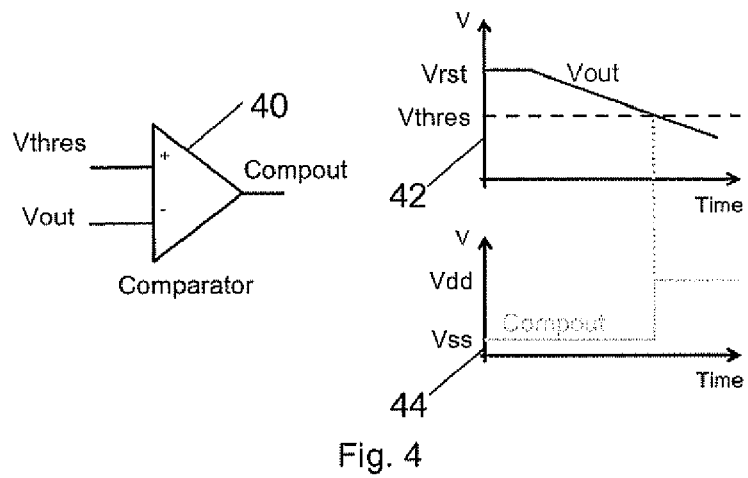
FIG. 4 is a schematic diagram illustrating a comparator and corresponding voltage graphs for readout of a data encoding pixel, e.g. as in FIG. 3.

Referring to FIG. 3, a cross section of two identification pixels 30 and 32 is shown. In this case, an opaque material 34 has been deposited over the photosensing portion of the pixel 32. When a light source 36 is illuminated over the pixels 30, 32, only pixel 30 detects the impinging light. FIG. 4 shows a comparator 40 connected to the output Vout of pixel 30 and a threshold voltage Vthres as shown in graph 42. The output voltage Vout of pixel 30 decreases from the reset voltage Vrst in the presence of light and when it reaches the threshold voltage the output of the comparator 40, as shown in graph 44, goes to high, indicating that pixel 30 is a binary one.

Figure 5:
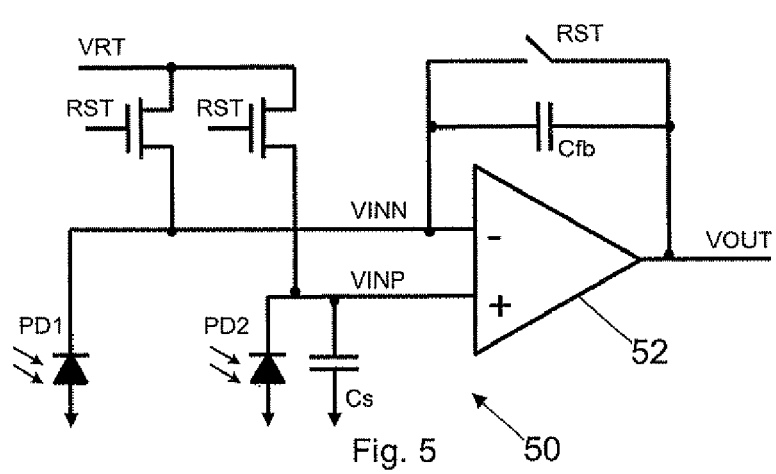
FIG. 5 is a schematic diagram illustrating a differential pixel architecture, which may be used as an identification pixel, e.g. as in FIG. 2.

Referring to FIG. 5, it is also possible for an ID pixel to use a different pixel architecture such as that disclosed in European patent application EP07270014.9, the specification of which is incorporated by reference. In this case the pixel 50 has two photodiodes PD1 and PD2. In this instance, either PD1 or PD2 would be covered by the bio-systems integrator depending on the intended output. That is, the bio-systems integrator would either cover PD1 or PD2 depending whether they wish to receive a high signal or a low signal at the output of the pixel. The polarity of the pixel depends on which photodiode is covered. If the photodiode attached to the negative terminal 52, which in this case is PD1, is covered and receives no light, while PD2 is uncovered and sensitive to light, the output readout of the opamp 52 will run down after re-set, which in this case is a mid-rail reset. If the photodiode attached to the positive terminal of the opamp 52, which in this case is PD2, is covered the output readout of the opamp 52 will ramp up after reset.

Figure 6:
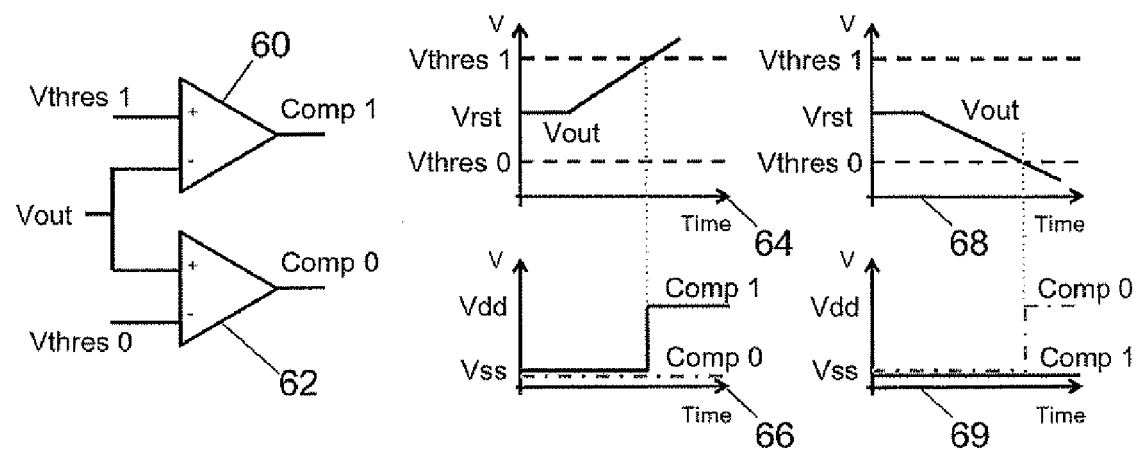
FIG. 6 is a schematic diagram illustrating comparators and corresponding voltage graphs for use with the differential pixel architecture of FIG. 5.

The output operation of the differential pixel of FIG. 5 is shown in FIG. 6. In this case two comparators 60 and 62 are connected to a first voltage threshold Vthres1, the output readout of the opamp 52 and a second voltage threshold Vthres0. If photodiode PD1 is uncovered the output readout ramps up crossing the first voltage threshold Vthres1 and giving a high output from comparator 60 and a low output from comparator 62. If photodiode PD2 is uncovered the output Vout of above opamp 52 shown in graph 68 in which the voltage drops from reset to cross with the second voltage threshold Vthres0. In this instance, the output of comparator 62 goes high and comparator 60 remains low as shown in graph 69.

Figure 7:
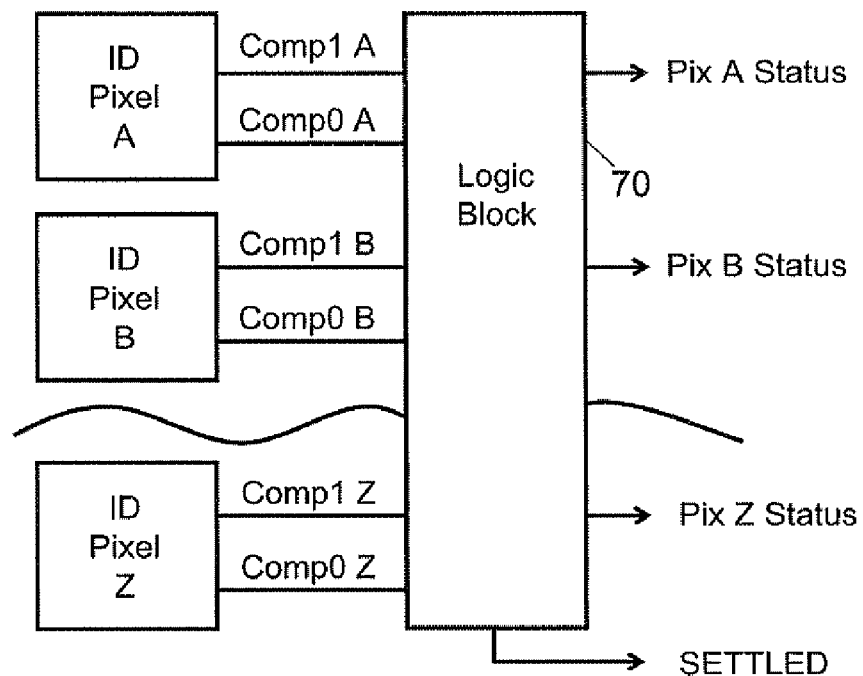
FIG. 7 is a block diagram illustrating a logic block which may be used to combine a number of data encoding pixels, e.g. as in FIG. 2.

It should be appreciated that, although the description above refers to a single pixel being used to represent either a high or low (binary 1 or 0), it is possible to use multiple pixels to represent each bit of information. As shown in FIG. 7, a logic block 70 can be used to AND together one or more pixels such that an output of high or low can be given for the whole group. The logic block 70 may incorporate logic which allows for a certain percentage of pixels to disagree with the other pixels to allow for tolerances in application of the opaque material. Similarly, it is not required that the bio-sensing pixels and data encoding pixels are physically separate on the image sensor. These may simply be designated areas on a "normal" image sensor pixel array.

In addition, the material deposited on the data encoding pixels does not have to be opaque. As long as the material has an opacity which allows the pixel to detect the differences between the presence of a material and the lack of presence of a material. It is possible that the bio-reagent material itself is appropriate for use as a material to cover data encoding pixels.

The image sensor may also be enabled to perform a self test of data encoded onto the data encoding pixels, according to a pre-determined scheme. For example, the image sensor could perform a "check sum" to verify a valid ID has been entered and output an error code if the self test fails. Furthermore, encoding data in this manner can be used to store any useful information. For example, an identification of the bio-reagent, batch number, date of production or expiry date.

Further modifications and improvements may be made without departing from the scope of the present invention.

That which is claimed is:

1. A method of encoding data on an image sensor, the image sensor comprising a plurality of pixels including at least one bio-sensing pixel and at least one data encoding pixel, the method comprising:
selectively applying a covering material to the at least one data encoding pixel based upon data to be encoded, the covering material having a detectable difference in opacity relative to no covering material being present;
reading the at least one data encoding pixel in the presence of light; and
decoding data based upon the presence of the covering material on the at least one data encoding pixel.

2. The method of claim 1, further comprising applying a biological reagent material to the at least one bio-sensing pixel.

3. The method of claim 2, wherein the covering material is the same as the biological reagent material.

4. The method of claim 3, further comprising performing a self-test by testing an operation of the biological reagent material concurrently with testing a validity of data obtained from the at least one data encoding pixel.

5. The method of claim 4, wherein testing the operation of the biological reagent material comprises detecting light emitted by the biological reagent material with the at least one data encoding pixel.

6. The method of claim 5, wherein testing the operation of the biological reagent material further comprises inferring the shelf-life of the biological reagent material based on a quantity of light emitted by the biological reagent material.

7. The method of claim 1, wherein reading further comprises comparing an output of the at least one data encoding pixel to a pre-determined threshold voltage, wherein outputs below the threshold voltage are considered to be a first digital value and outputs above the threshold voltage are considered to be a second digital value for a given pixel integration time.

8. The method of claim 1, wherein the at least one data encoding pixel comprises a plurality of data encoding pixels with each data encoding pixel representing a bit of a digital word.

9. The method of claim 1, wherein the at least one data encoding pixel comprises a plurality of data encoding pixels with groups of data encoding pixels represent a bit of a digital word.

10. The method of claim 1, wherein the data to be encoded includes at least one of identification information, batch information, date of deposit of bio-reagent material, expiration date, operation of image sensor information, integration time of image sensor, micro-fluidic control information, and biological test information.

11. The method of claim 1, further comprising performing a self-test with respect to the at least one data encoding pixel.

12. The method of claim 11, wherein performing the self-test further comprises testing whether the data obtained from the at least one data encoding pixel is valid based on a scheme.

13. The method of claim 12, wherein the scheme includes the use of a checksum value and testing further comprises comparing the obtained data with an expected checksum value.

14. The method of claim 1, wherein the covering material is opaque.

15. An image sensor comprising:
a plurality of pixels comprising at least one bio-sensing pixel and at least one data encoding pixel;
readout circuitry to read output pixel values from the plurality of pixels;
determination circuitry to determine whether the at least one data encoding pixel is covered by a covering material based on an output pixel value of the at least one data encoding pixel and, based thereon, outputting encoded data; and
decoding circuitry to decode the encoded data.

16. The image sensor of claim 15, wherein the at least one data encoding pixel comprises a differential pixel architecture.

17. The image sensor of claim 15, wherein the determination circuitry comprises a comparator to compare at least one threshold voltage with the output pixel value.

18. The image sensor of claim 15, wherein the at least one data encoding pixel comprises a plurality of data encoding pixels with each data encoding pixel representing a bit of a digital word.

19. The image sensor of claim 15, wherein the at least one data encoding pixel comprises a plurality of data encoding pixels with groups of data encoding pixels represent a bit of a digital word.

20. A bio-optical sensor system comprising an image sensor including:
a plurality of pixels comprising at least one bio-sensing pixel and at least one data encoding pixel;
readout circuitry to read output pixel values from the plurality of pixels;
determination circuitry to determine whether the at least one data encoding pixel is covered by a covering material based on an output pixel value of the at least one data encoding pixel and, based thereon, outputting encoded data; and
decoding circuitry to decode the encoded data.

21. The bio-optical sensor system of claim 20, wherein the at least one data encoding pixel comprises a differential pixel architecture.

22. The bio-optical sensor system of claim 20, wherein the determination circuitry comprises a comparator to compare at least one threshold voltage with the output pixel value.

23. The bio-optical sensor system of claim 20, wherein the at least one data encoding pixel comprises a plurality of data encoding pixels with each data encoding pixel representing a bit of a digital word.

24. The bio-optical sensor system of claim 20, wherein the at least one data encoding pixel comprises a plurality of data encoding pixels with groups of data encoding pixels represent a bit of a digital word.

* * * * *